United States Patent
Khachik

(10) Patent No.: US 9,580,371 B2
(45) Date of Patent: Feb. 28, 2017

(54) PROCESS FOR SIMULTANEOUS EXTRACTION AND SEPARATION OF ESTERIFIED AND UNESTERIFIED MONOHYDROXYCAROTENOIDS

(71) Applicant: University of Maryland, College Park, College Park, MD (US)

(72) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/891,496

(22) PCT Filed: May 16, 2014

(86) PCT No.: PCT/US2014/038353
§ 371 (c)(1),
(2) Date: Nov. 16, 2015

(87) PCT Pub. No.: WO2014/186680
PCT Pub. Date: Nov. 20, 2014

(65) Prior Publication Data
US 2016/0122268 A1 May 5, 2016

Related U.S. Application Data

(60) Provisional application No. 61/824,136, filed on May 16, 2013.

(51) Int. Cl.
*C07C 29/84* (2006.01)
*B01D 9/00* (2006.01)
*B01D 11/02* (2006.01)

(52) U.S. Cl.
CPC .............. *C07C 29/84* (2013.01); *A23L 5/44* (2016.08); *B01D 9/00* (2013.01); *B01D 11/0219* (2013.01);
(Continued)

(58) Field of Classification Search
CPC ....... A23L 5/44; C07C 29/84; A23V 2002/00; B01D 11/0219; B01D 11/0296; B01D 9/00; B01D 2009/0086; A61K 2236/00
See application file for complete search history.

(56) References Cited

U.S. PATENT DOCUMENTS 6,262,284 B1  7/2001  Khachik
6,911,564 B2  6/2005  Khachik
(Continued)

FOREIGN PATENT DOCUMENTS

WO    WO 99/54408 A1    10/1999
WO    WO 02/060865 A1    8/2002
WO    WO 02/094772 A1    11/2002

OTHER PUBLICATIONS

Kale, A. V. et al. "Rapid analysis of Xanthophylls in Ethanol Extracts of Corn by HPLC" J. Liq. Chromat. & Related Technologies 2007, 30, pp. 1093-1104.*
(Continued)

*Primary Examiner* — Paul A Zucker
*Assistant Examiner* — Medhanit Bahta
(74) *Attorney, Agent, or Firm* — Sterne, Kessler, Goldstein & Fox P.L.L.C.

(57) ABSTRACT

The present invention is in the field of organic and natural product chemistry. The present invention relates to an efficient process for purification, simultaneous extraction, and separation of monohydroxycarotenoids from dihydroxycarotenoids in various natural products or in synthetic mixtures. Similarly, the process can also be applied to the simultaneous extraction, saponification, and separation of esterified mono- and dihydroxycarotenoids in natural products and their oleoresins or in their synthetic mixtures. Therefore, esterified and unesterified monohydroxycarotenoids such as (3R)-β-cryptoxanthin and (3R,6'R)-α-cryptoxanthin can be efficiently separated from their correspond-
(Continued)

ing dihydroxycarotenoids such as (3R,3'R,6'R)-lutein and (3R,3'R)-zeaxanthin that are found in various plants or in synthetic mixtures.

18 Claims, 3 Drawing Sheets

(52) U.S. Cl.
CPC ...... *B01D 11/0296* (2013.01); *A23V 2002/00* (2013.01); *A61K 2236/00* (2013.01); *B01D 2009/0086* (2013.01)

(56) References Cited

U.S. PATENT DOCUMENTS 7,297,803 B2 * 11/2007 Madhavi ................ C09B 61/00
554/12
8,425,948 B2 * 4/2013 Sethuraman .......... C07C 403/24
424/725

OTHER PUBLICATIONS

International Search Report for International Application No. PCT/US14/38353, United States Patent and Trademark Office, United States, mailed on Sep. 4, 2014.

Supplementary Partial European Search Report for European Application No. EP 14 79 7066, Munich, Germany, mailed on Dec. 9, 2016.

* cited by examiner

FIGURE 1

A. Dihydroxycarotenoids

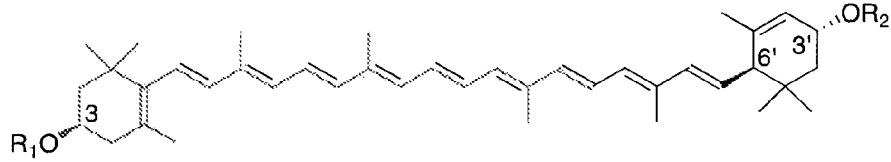

R₁ = R₂ = H, (3R,3'R,6'R)-lutein (1)
R₁ = R₂ = CH₃(CH₂)₁₂CO, (3R,3'R,6'R)-lutein dimyristate (2)
R₁ = R₂ = CH₃(CH₂)₁₄CO, (3R,3'R,6'R)-lutein dipalmitate (3)
R₁ = R₂ = CH₃CO, (3R,3'R,6'R)-lutein diacetate (4)

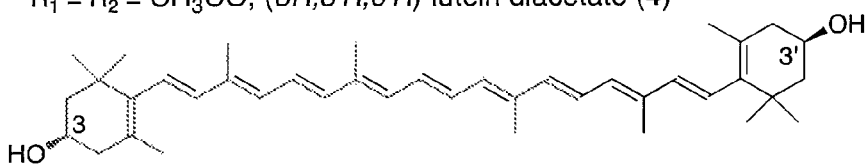

R₁ = R₂ = H, (3R,3'R)-zeaxanthin (5)
R₁ = R₂ = CH₃(CH₂)₁₂CO, (3R,3'R)-zeaxanthin dimyristate (6)
R₁ = R₂ = CH₃(CH₂)₁₄CO, (3R,3'R)-zeaxanthin dipalmitate (7)
R₁ = R₂ = CH₃CO, (3R,3'R)-zeaxanthin diacetate (8)

B. Monohydroxycarotenoids

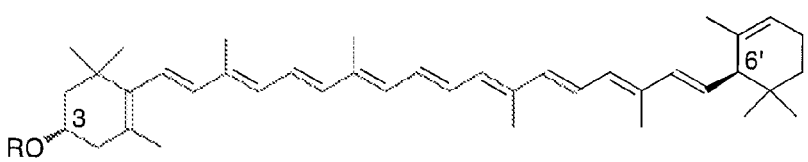

R = H, (3R,6'R)-α-cryptoxanthin (9)
R = CH₃(CH₂)₁₂CO, (3R,6'R)-α-cryptoxanthin myristate (10)
R = CH₃(CH₂)₁₄CO, (3R,6'R)-α-cryptoxanthin palmitate (11)
R = CH₃CO, (3R,6'R)-α-cryptoxanthin acetate (12)

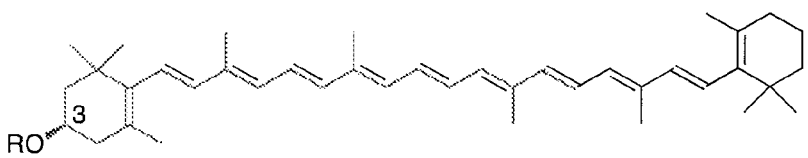

R = H, (3R)-β-cryptoxanthin (13)
R = CH₃(CH₂)₁₂CO, (3R)-β-cryptoxanthin myristate (14)
R = CH₃(CH₂)₁₄CO, (3R)-β-cryptoxanthin palmitate (15)
R = CH₃CO, (3R)-β-cryptoxanthin acetate (16)

PROCESS FOR SIMULTANEOUS EXTRACTION AND SEPARATION OF ESTERIFIED AND UNESTERIFIED MONOHYDROXYCAROTENOIDS

BACKGROUND OF THE INVENTION

Field of Invention

The present invention is in the field of organic and natural product chemistry. The present invention relates to an efficient process for purification, simultaneous extraction, and separation of monohydroxycarotenoids from dihydroxycarotenoids in various natural products or in synthetic mixtures. Similarly, the process can also be applied to the simultaneous extraction, saponification, and separation of esterified mono- and dihydroxycarotenoids in natural products and their oleoresins or in their synthetic mixtures. Therefore, esterified and unesterified monohydroxycarotenoids such as (3R)-β-cryptoxanthin and (3R,6'R)-α-cryptoxanthin can be efficiently separated from their corresponding dihydroxycarotenoids such as (3R,3'R,6'R)-lutein and (3R,3'R)-zeaxanthin that are found in various plants or in synthetic mixtures.

Background Art (3R)-β-Cryptoxanthin, (3R,6'R)-α-cryptoxanthin, (3R,3'R,6'R)-lutein, and (3R,3'R)-zeaxanthin are among the 12 major dietary carotenoids which are found in human serum, milk, major organs, and tissues. In view of the biological activity of carotenoids in the prevention of chronic diseases such as cancer, age-related macular degeneration, and cardiovascular disease, industrial production of a wide range of purified carotenoids is of great importance. Numerous processes have been reported for the extraction and isolation of these carotenoids from plants and synthetic mixtures. However, according to all of these processes the purified carotenoid product consists of a mixture of mono- and dihydroxycarotenoids in varying compositions. Therefore, to this date there is no reported process that allows for the simultaneous extraction, saponification, separation, and purification of these carotenoids from plants or synthetic mixtures. In most cases, these carotenoids are present in plants and natural products in their esterified forms with fatty acids such as myristic and palmitic acids. The chemical structures of monohydroxycarotenoids, (3R)-β-cryptoxanthin and (3R,6'R)-α-cryptoxanthin, and dihydroxycarotenoids, (3R,3'R,6'R)-lutein and (3R,3'R)-zeaxanthin, are shown in FIG. 1. The chemical structure of mono- and diacetates of these carotenoids that are typically prepared by partial synthesis from these carotenoids are also shown in FIG. 1.

Numerous processes have been reported in which plants are first extracted to obtain an oleoresin that is subsequently saponified to yield the unesterified form of these carotenoids. The unesterified forms of these carotenoids are then subjected to crystallization and purification for use as nutritional supplements. However, these purified carotenoids consist of varying compositions of mono- and dihydroxycarotenoids. For example, plants that are predominantly rich in (3R,3'R,6'R)-lutein also have minor quantities of (3R,6'R)-α-cryptoxanthin and plants that are abundant in (3R,3'R)-zeaxanthin contain minor levels of (3R)-β-cryptoxanthin.

Because mono- and dihydroxycarotenoids exhibit different biological activities with regard to their nutritional benefits, the separation of each of these individual carotenoids is of great importance. The present invention describes efficient processes for the purification, simultaneous extraction, and saponification, as well as for the separation of monohydroxycarotenoids from dihydroxycarotenoids.

BRIEF SUMMARY OF THE INVENTION

In some embodiments, the present invention provides a method of at least partially separating at least one monohydroxycarotenoid ester from at least one dihydroxycarotenoid ester, comprising continuously extracting the at least one monohydroxycarotenoid ester from a mixture of the at least one monohydroxycarotenoid ester and the at least one dihydroxycarotenoid ester with an alcohol to give an alcoholic solution enriched in the at least one monohydroxycarotenoid ester.

In some embodiments, the method further comprises concentrating the alcoholic solution to give a residue enriched in the at least one monohydroxycarotenoid ester.

In some embodiments, the at least one monohydroxycarotenoid ester residue is subjected to further continuous extraction with an alcohol to give an alcoholic solution enriched in the at least one monohydroxycarotenoid ester.

In some embodiments, the method further comprises concentrating the alcoholic solution to give a residue further enriched in the at least one monohydroxycarotenoid ester.

In some embodiments, the method further comprises subjecting the residue further enriched in the at least one monohydroxycarotenoid ester to saponification to give an at least one monohydroxycarotenoid.

In some embodiments, the method further comprises crystallization of the solution enriched in the at least one monohydroxycarotenoid ester.

In some embodiments, the crystallization occurs in a solvent, wherein the solvent is a mixture of a hydrocarbon and an alcohol or acetone and an alcohol.

In some embodiments, the continuous extraction is carried out by Soxhlet extraction.

In some embodiments, the continuous extraction is carried out simultaneously with saponification.

In some embodiments, the mixture of the at least one monohydroxycarotenoid ester and the at least one dihydroxycarotenoid ester is present in the petals of marigold flowers.

In some embodiments, the mixture of the at least one monohydroxycarotenoid ester and the at least one dihydroxycarotenoid ester is present in Chinese Lycium mill.

In some embodiments, the at least one monohydroxycarotenoid ester is (3R)-β-cryptoxanthin esters.

In some embodiments, the at least one monohydroxycarotenoid ester is (3R)-β-cryptoxanthin esters and the at least one dihydroxycarotenoid ester is (3R,3'R)-zeaxanthin esters.

In some embodiments, the at least one monohydroxycarotenoid ester is (3R,6'R)-α-cryptoxanthin esters and the at least one dihydroxycarotenoid ester is (3R,3'R,6'R)-lutein esters.

In some embodiments, the at least one monohydroxycarotenoid is (3R)-β-cryptoxanthin.

In some embodiments, the alcohol is methanol, ethanol, or 2-propanol.

In some embodiments, the esters are myristates, palmitates, acetates, or mixtures thereof.

In some embodiments, the present invention provides a method of at least partially separating at least one monohydroxycarotenoid from at least one dihydroxycarotenoid, comprising continuously extracting the at least one monohydroxycarotenoid from a mixture of the at least one monohydroxycarotenoid and the at least one dihydroxycarotenoid with a hydrocarbon to give a hydrocarbon solution enriched in the at least one monohydroxycarotenoid.

In some embodiments, the method further comprises concentrating the hydrocarbon solution to give a residue enriched in the at least one monohydroxycarotenoid.

In some embodiments, the at least one monohydroxycarotenoid residue is subjected to further continuous extraction with a hydrocarbon to give a hydrocarbon solution enriched in the at least one monohydroxycarotenoid.

In some embodiments, the method further comprises concentrating the hydrocarbon solution to give a residue further enriched in the at least one monohydroxycarotenoid.

In some embodiments, the continuous extraction is carried out by Soxhlet extraction.

In some embodiments, the at least one monohydroxycarotenoid is (3R)-β-cryptoxanthin and the at least one dihydroxycarotenoid is (3R,3'R)-zeaxanthin.

In some embodiments, the at least one monohydroxycarotenoid is (3R,6'R)-α-cryptoxanthin and the at least one dihydroxycarotenoid is (3R,3'R,6'R)-lutein.

In some embodiments, the at least one monohydroxycarotenoid is (3R)-β-cryptoxanthin.

In some embodiments, the hydrocarbon is pentane or hexane.

BRIEF DESCRIPTION OF THE FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention. The following drawings are given by way of illustration only, and thus are not intended to limit the scope of the present invention.

FIG. 1 provides chemical structures of (A) the dihydroxycarotenoids (3R,3'R,6'R)-lutein dimyristate (2), (3R,3'R,6'R)-lutein dipalmitate (3), (3R,3'R,6'R)-lutein diacetate (4), (3R,3'R)-zeaxanthin (5), (3R,3'R)-zeaxanthin dimyristate (6), (3R,3'R)-zeaxanthin dipalmitate (7), and (3R,3'R)-zeaxanthin diacetate (8); and (B) the monohydroxycarotenoids (3R,6'R)-α-cryptoxanthin (9), (3R,6'R)-α-cryptoxanthin myristate (10), (3R,6'R)-α-cryptoxanthin palmitate (11), (3R,6'R)-α-cryptoxanthin acetate (12), (3R)-β-cryptoxanthin (13), (3R)-β-cryptoxanthin myristate (14), (3R)-β-cryptoxanthin palmitate (15), and (3R)-β-cryptoxanthin acetate (16).

DETAILED DESCRIPTION OF THE INVENTION

As used herein, the term "partially separating" means that at least 70% of the undesired product is removed from the desired product. In some embodiments, partially separating means that at least 75%, at least 80%, at least 85%, at least 90%, at least 95%, or at least 98% of the undesired product is removed from the desired product. In some embodiments, the partially separated product is at least 75%, at least 80%, at least 85%, at least 90%, at least 95%, or at least 98% pure. In some embodiments, the partially separated product is at least 98% pure.

As used herein, the singular terms "a" and "the" are synonymous and used interchangeably with "at least one," unless the language and/or context clearly indicate otherwise.

As used herein, the term "comprising" means including, made up of, and composed of.

The present invention provides processes for the separation of monohydroxycarotenoids from dihydroxycarotenoids. According to the first strategy, carotenoid esters in plants or synthetic samples are simultaneously extracted and saponified by Soxhlet extraction in the first step. This is followed by binary crystallization or a second Soxhlet extraction that allows the separation of these carotenoids. This strategy is shown in FIG. 2.

Figure 2:
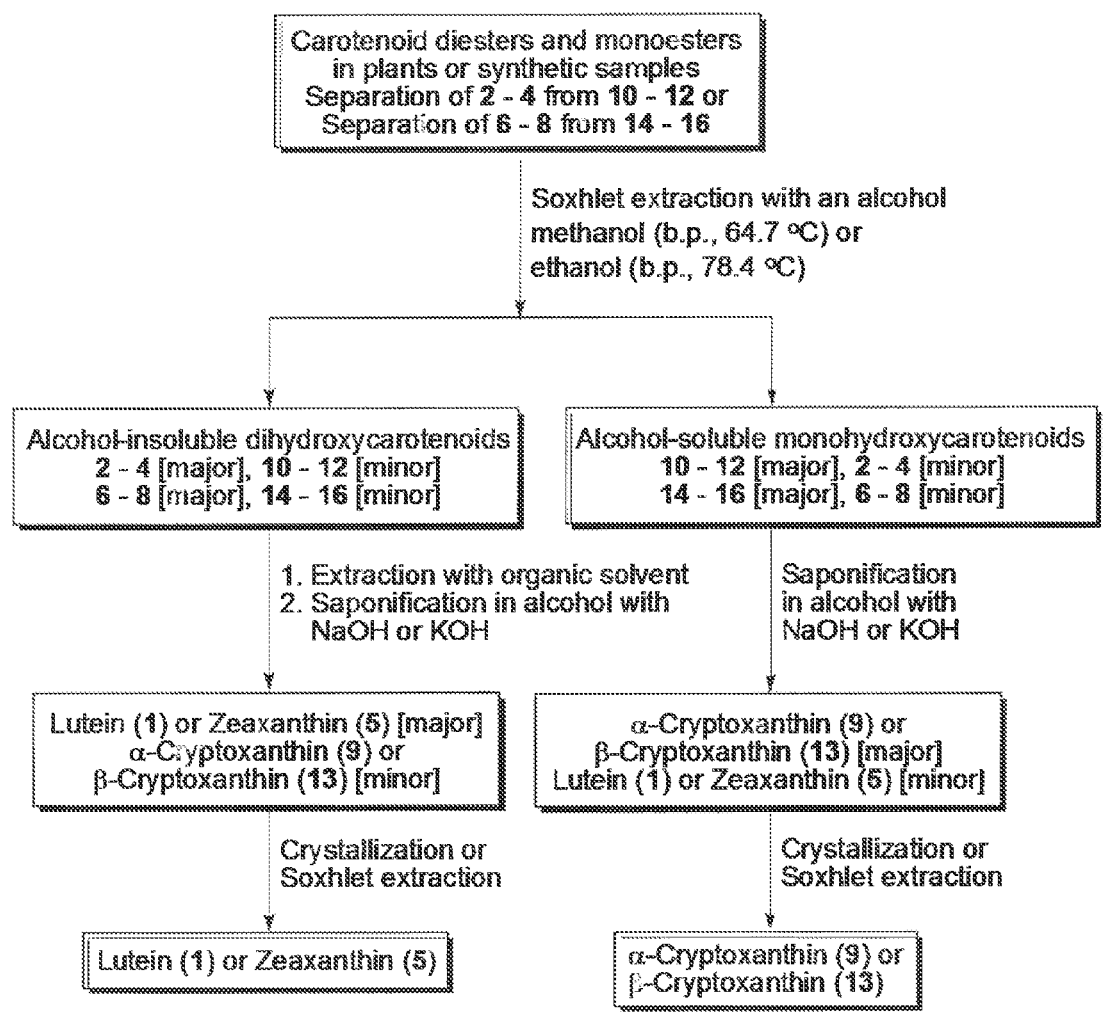
FIG. 2 is a schematic representation of the separation of mono- and dihydroxycartenoid esters by Soxhlet extraction followed by saponification resulting in the complete separation of lutein (1) or zeaxanthin (5) from α-cryptoxanthin (9) or β-cryptoxanthin (13).

It should be noted that while dihydroxycarotenoids are well separated from monohydroxycarotenoids by the process shown in FIG. 2, separation of dihydroxycarotenoids such as lutein and zeaxanthin from each other is not possible by this strategy. Similarly, this process cannot be applied to the separation of monohydroxycarotenoids such as α-cryptoxanthin and β-cryptoxanthin.

Based on this process, it has been discovered that there is a differential solubility between dihydroxycarotenoids such as lutein or zeaxanthin diesters when compared to monohydroxycarotenoids such as α-cryptoxanthin or β-cryptoxanthin esters. Therefore, when these carotenoids are subjected to Soxhlet extraction with an alcohol such as ethanol or methanol, carotenoid monoesters, due to their superior solubility in alcohols, are extracted while carotenoid diesters for the most part remain insoluble. Therefore, this strategy can be applied to separate dihydroxycarotenoids from monohydroxycarotenoids. Therefore, Soxhlet extraction with an alcohol (e.g, methanol or ethanol) can result in removal of esters of monohydroxycarotenoids (10-12, 14-16) while esters of dihydroxcarotenoids (2-4, 6-8) for the most part remain insoluble in alcohol. The alcohol insoluble fraction is then extracted from the plant material by an organic solvent (e.g., pentane, hexane, acetone, ethyl acetate, diethyl ether, tert-butyl methyl ether, or tetrahydrofuran) and after solvent evaporation is then saponified in an alcohol to give lutein (1) or zeaxanthin (5) as the major product and α-cryptoxanthin (9) or 3-cryptoxanthin (13) as the minor product. Further crystallization or Soxhlet extraction of this mixture can then result in complete separation of 1 or 5 from 9 or 13, respectively. Similarly, the esters of monohydroxycarotenoids (10-12, 14 . . . 16) that are removed by Soxhlet extraction are accompanied by minor quantities of dihydroxycarotenoids 2-4 and 6-8. These carotenoids are saponified with alcoholic solution of NaOH or KOH and are subsequently subjected to crystallization or Soxhlet extraction to yield α-cryptoxanthin (9) or β-cryptoxanthin (13).

In some embodiments, the alcohol is methanol, ethanol, 2-propanol, or combinations thereof.

In some embodiments, the organic solvent is pentane, hexane, acetone, ethyl acetate, diethyl ether, tert-butyl methyl ether, tetrahydrofuran, or combinations thereof.

The binary crystallization of a mixture of mono- and dihydroxycarotenoids from a hydrocarbon solvent (pentane, hexane) and an alcohol (methanol, ethanol) can also result in separation of these carotenoids. Monohydroxycarotenoids are solubilized in binary solvents while the dihydroxycarotenoids remain only sparingly soluble. Consequently, close to 90% of the dihydroxycarotenoids (lutein or zeaxanthin) are separated in crystalline form and are accompanied by only 10% of monohydroxycarotenoids. Conversely, the filtrate from crystallization contains monohydroxycarotenoids (α-cryptoxanthin or β-cryptoxanthin) and minor quantities of dihydroxycarotenoids (lutein or zeaxanthin). Binary crystallization can also be carried out with combinations of a hydrocarbon solvent and acetone or acetone and an alcohol to produce the same results. If needed, a second crystallization using the fore-mentioned binary solvents is carried out to achieve the complete separation of mono- and dihydroxycarotenoids.

In some embodiments, the solvent for crystallization is methanol, ethanol, 2-propanol, pentane, hexane, acetone, ethyl acetate, diethyl ether, tert-butyl methyl ether, tetrahydrofuran, or combinations thereof. In some embodiments, the solvent for crystallization is pentane and acetone, hexane and acetone, methanol and acetone, ethanol and acetone, or 2-pentanol and acetone.

In an alternative process, Soxhlet extraction of mono- and dihydroxycarotenoids can also be carried out to separate these carotenoids. As mentioned earlier, esterified forms of lutein and zeaxanthin are well solubilized in hydrocarbon solvents such as n-hexane and n-pentane, whereas their unesterified parent compounds, α-cryptoxanthin or β-cryptoxanthin, show a remarkable difference in their solubility behavior and remain insoluble. In fact, α-cryptoxanthin or β-cryptoxanthin are considerably more soluble in n-pentane or n-hexane than lutein and zeaxanthin.

For example, the present invention has demonstrated that Soxhlet extraction of a mixture of lutein and α-cryptoxanthin with n-pentane or n-hexane can be used to effectively separate these carotenoids. This is because α-cryptoxanthin shows a much greater solubility than lutein and is removed from the mixture by Soxhlet extraction. Similarly, a mixture of zeaxanthin and β-cryptoxanthin can be separated by Soxhlet extraction with n-pentane or n-hexane due to their differential solubility in hydrocarbon solvents.

Figure 3:
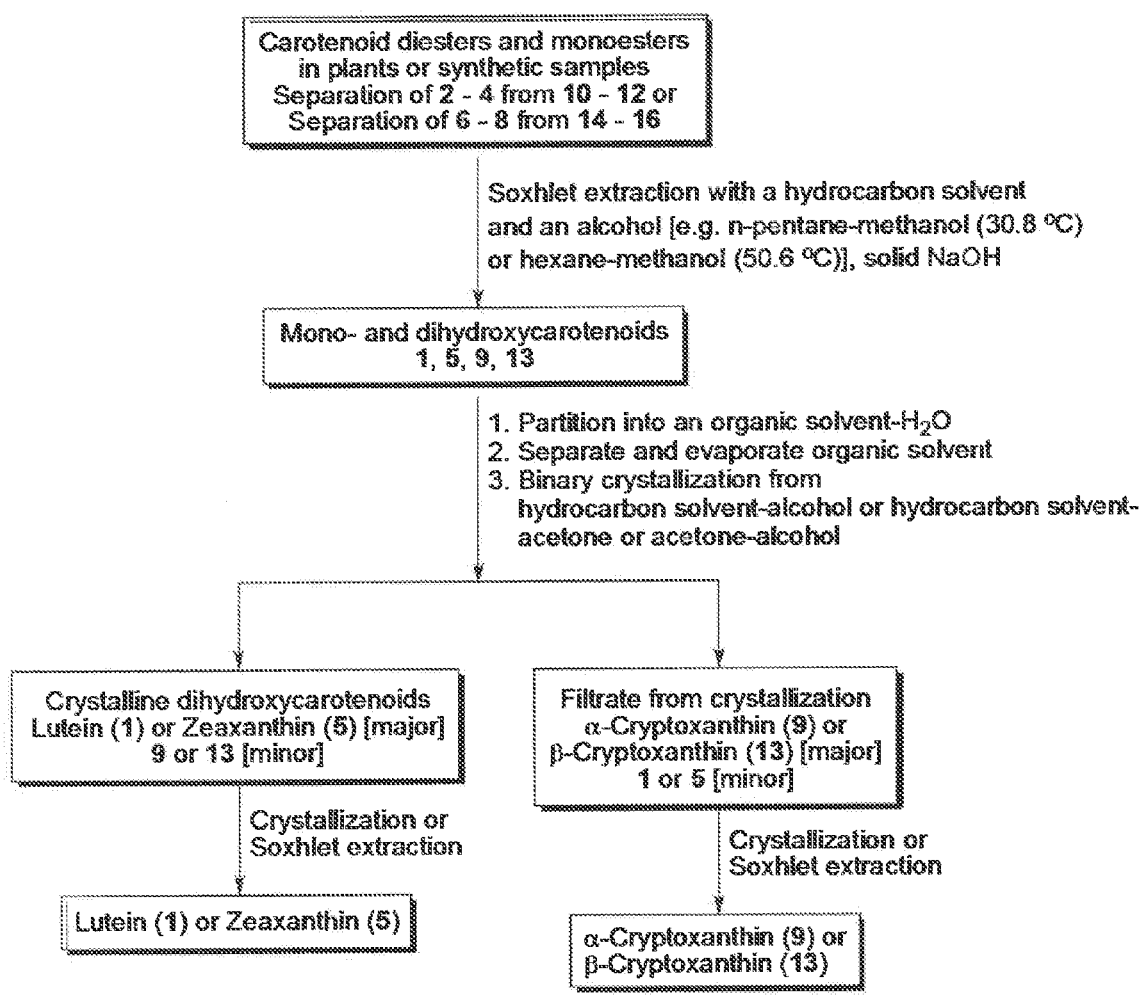
FIG. 3 is a schematic representation of the simultaneous extraction and saponification of esterified carotenoids (lutein, zeaxanthin, α-cryptoxanthin, and β-cryptoxanthin) followed by separation of dihydroxycartenoids (lutein (1) or zeaxarithin (5)) from monohydroxycartenoids (α-cryptoxanthin (9) or β-cryptoxanthin (13)).

To further simplify this process, the separation of monhydroxycarotenoids from dihydroxycarotenoids can be achieved at a later stage after these carotenoids are extracted and simultaneously saponified. Because carotenoid monoesters and carotenoid diesters are soluble in hydrocarbon solvents such as n-pentane and hexane, combination of these solvents with an alcohol can be used to extract these carotenoids from plants or synthetic samples. Therefore, as shown in FIG. 3, a binary mixture of an alcohol and a hydrocarbon is used for extraction of carotenoid esters in the presence of solid NaOH or KOH. This simultaneous extraction and saponification cannot be applied to direct conventional extraction of carotenoid esters. This is because once the plant materials are exposed to basic conditions, numerous by-products and impurities are generated and significant quantities of base would be needed to complete the saponification. In many cases, the high concentration of base also results in degradation of carotenoids. However, in simultaneous Soxhlet extraction and saponification, the plant material does not come into contact with the base and saponification is carried out with the extracted carotenoid esters.

Several combinations of solvents can be used with this process consisting of a hydrocarbon such as n-pentane or n-hexane with an alcohol such as methanol, ethanol, or 2-propanol. Various combinations of these solvents produce azeotropes that allow the simultaneous extraction and saponification of carotenoid esters at various temperatures by Soxhlet extraction. The combinations of these solvents that can be used with this process are shown in Table 1.

TABLE 1

Various combinations of n-pentane and n-hexane that form azeotropes with alcohols can be used in simultaneous extraction and saponification of carotenoid esters from plants and synthetic samples by Soxhlet extraction.

| Azeotropes of n-pentane and n-hexane with alcohols | Boiling point of mixture at atmospheric pressure |
|---|---|
| n-pentane (b.p. = 36.2° C.)/methanol (b.p. = 64.7° C.) | 30.8° C. |
| n-pentane (b.p. = 36.2° C.)/ethanol (b.p. = 78.4° C.) | 34.3° C. |
| n-pentane (b.p. = 36.2° C.)/2-propanol (b.p. = 82.5° C.) | 35.5° C. |
| n-hexane (b.p. = 68.9° C.)/methanol (b.p. = 64.7° C.) | 50.6° C. |
| n-hexane (b.p. = 68.9° C.)/ethanol (b.p. = 78.4° C.) | 58.7° C. |
| n-hexane (b.p. = 68.9° C.)/2-propanol (b.p. = 82.5° C.) | 62.7° C. |

For example, n-pentane and methanol (1:1, v:v) form a binary azeotrope boiling at 30.8° C. At the boiling point of the mixture 91 wt % of n-pentane is distilled as opposed to 9 wt. % of methanol. Similarly, a mixture of n-hexane and methanol (1:1, v:v) forms a binary azeotrope boiling at 50.6° C. At the boiling point of the mixture, 72 wt % of n-hexane is distilled and 28 wt % of methanol. Alternatively, a combinations of these hydrocarbons with ethanol or 2-propanol can be employed with this process.

In some embodiments, the solvent for simultaneous Soxhlet extraction and saponification is methanol, ethanol, 2-propanol, pentane, hexane, diethyl ether, tert-butyl methyl ether, tetrahydrofuran, or combinations thereof. In some embodiments, the solvent for simultaneous Soxhlet extraction and saponification is pentane and methanol, pentane and ethanol, pentane and 2-propanol, hexane and methanol, hexane and ethanol, or hexane and 2-propanol.

Therefore, the saponification with this technique can be carried out simultaneously in the same reactor or once the extraction is completed, the solid NaOH can be added to begin the saponification. The advantage of using solid NaOH is because exposure of carotenoids at high concentration to base can result in degradation of these compounds. Because the added NaOH or KOH is gradually dissolved in alcohol (MeOH or EtOH), the saponification can be carried out under mild conditions within 2 to 3 hours. At the end of saponification, the solvents are removed and the saponified carotenoids are partitioned between an organic solvent such as ethyl acetate and water. The organic phase is removed and evaporated to dryness and is subjected to binary crystallization from a hydrocarbon (n-pentane or n-hexane) and an alcohol (methanol, ethanol, 2-propanol) or combination of acetone with the forementioned alcohols to separate monohydroxycarotenoids from dihydroxycarotenoids as described earlier.

An alternative approach to the process shown in FIG. 3 is to first extract the plant material by conventional extraction followed by saponification to obtain a mixture of mono- and dihydroxycarotenoids. This mixture can then be subjected to binary crystallization or Soxhlet extraction to separate carotenoid monoesters from diesters as previously described.

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

EXPERIMENTAL

Sources of Mono- and Dihydroxycarotenoids

Two major plant sources of esterified carotenoids were employed: the petals of marigold flowers (*Tagete erecta*) and a Chinese fruit known as Lycium mill that was purchased from a local Chinese supermarket. The composition of carotenoids in marigold flower petals was: lutein (1, 96%), zeaxanthin (5, 3.5%), and α-cryptoxanthin (9, 0.5%). Chinese Lycium mill contained mainly zeaxanthin (5, 98.7%), and β-cryptoxanthin (13, 1.3%). α-Cryptoxanthin acetate (12), β-cryptoxanthin acetate (16), and zeaxanthin (5) were prepared by partial or total synthesis according to known procedures. Commercially available lutein was obtained from Kemin Health (Des Moines, Iowa).

Example 1

Extraction and Separation of (3R,6'R)-α-Cryptoxanthin Monoesters from Lutein Diesters in Marigold Flowers (*Tagete erecta*)

The petals of marigold flowers (*Tagete erecta*) typically consist of lutein diesters 2 and 3 and their crossed esters (96%), zeaxanthin diesters 6 and 7 and their crossed esters (3.5%), and (3R,6'R)-α-cryptoxanthin esters 10 and 11 (0.5%). The objective of this experiment was to demonstrate that even though 10 and 11 are present in very minor quantities, these monohydroxycarotenoid esters could be separated from dihydroxycarotenoids 2, 3, 6, and 7.

50 g of marigold petals were transferred into a Soxhlet extraction apparatus and were extracted with methanol (b.p.=64.7° C.) or ethanol (b.p.=78.4° C.). The diesters of lutein and zeaxanthin are only sparingly soluble in alcohols while the monoesters have a slightly better solubility in these solvents. Therefore, conventional extraction with these alcohols is not economical because large quantities of alcohol would have to be used to extract only minor amounts of carotenoids. However, in the Soxhlet extraction, the solvent is continuously recycled and large volumes of the solvent is not needed. Further, due to their differential solubility, diesters of dihydroxycarotenoids 2, 3, 6, and 7 were only partially extracted while all of the carotenol monohydroxycarotenoid esters 10 and 11 were extracted into methanol or ethanol within several hours. The composition of the extract after 4 hours was: lutein diesters (10%), zeaxanthin diesters (0.5%), and (3R,6'R)-α-cryptoxanthin monoesters 10 and 11 (89.5%).

After solvent evaporation under reduced pressure, the residue was subjected to a second Soxhlet extraction to obtain (3R,6'R)-α-cryptoxanthin monoesters 10 and 11 in 98% purity. These monoesters were then subjected to saponification according to the known methods to yield (3R,6'R)-α-cryptoxanthin (9).

Example 2

Extraction and Separation of (3R)-β-Cryptoxanthin Monoesters from Zeaxanthin Diesters in Chinese Lycium Mill Chinese Lycium mill typically consists of zeaxanthin diesters 6 and 7 and their crossed esters (98.7%) and (3R)-β-cryptoxanthin esters 14 and 15 (1.3%). The objective of this experiment was to simultaneously extract and separate 14 and 15 from zeaxanthin diesters 6 and 7. The same solubility principle that was applied to the extraction and separation of (3R,6'R)-α-cryptoxanthin esters from lutein diesters was also applied to the separation of (3R)-β-cryptoxanthin esters from zeaxanthin diesters.

50 g of Chinese Lycium mill was transferred into a Soxhlet extraction apparatus and was extracted with boiling methanol (b.p.=64.7° C.) or ethanol (b.p.=78.4° C.). Because of their differential solubility, diesters of zeaxanthin 6 and 7 were only partially extracted while all of the (3R)-β-cryptoxanthin esters 14 and 15 were extracted into methanol and ethanol within several hours. The composition of the extract after 4 hours was: zeaxanthin diesters (12%) and (3R)-β-cryptoxanthin esters 14 and 15 (88%)

After solvent evaporation under reduced pressure, the residue was subjected to a second Soxhlet extraction to obtain (3R)-β-cryptoxanthin esters 14 and 15 in 98% purity. These monoesters were then subjected to saponification according to known methods to yield (3R)-β-cryptoxanthin (13).

Example 3

Separation of Synthetic (3R,3'R)-Zeaxanthin Diacetate from (3R)-β-Cryptoxanthin Acetate The above Soxhlet extraction was also successfully applied to the separation of a synthetic mixture of (3R,3'R)-zeaxanthin diacetate (8) and (3R)-β-cryptoxanthin acetate (16). 100 mg a 50% mixture of 8 and 16 was extracted in a Soxhlet apparatus with boiling methanol or ethanol. The composition of the extract after 3 hours was: 80% of 16 and 20% of 8. In a subsequent Soxhlet extraction with methanol or ethanol, 16 was obtained in 98% purity.

Example 4

Separation of (3R)-β-Cryptoxanthin from (3R,3'R)-Zeaxanthin by Soxhlet Extraction 100 mg of 1:1 mixture of (3R)-β-cryptoxanthin (13) and (3R,3'R)-zeaxanthin (5) was subjected to Soxhlet extraction and these unesterified carotenoids were extracted with boiling pentane (b.p.=36° C.) or hexane (b.p.=69° C.). (3R,3'R)-zeaxanthin was only sparingly soluble in these hydrocarbon solvents while (3R)-β-cryptoxanthin showed significantly better solubility. After 4 hours, the composition of the extract was: (3R)-β-cryptoxanthin (13) (85%) and (3R,3'R)-zeaxanthin (5) (15%). In a subsequent Soxhlet extraction with pentane or hexane, (3R)-β-cryptoxanthin (13) was obtained in 98% purity.

Example 5

Separation of (3R)-β-Cryptoxanthin from (3R,3'R)-Zeaxanthin by Crystallization 100 mg of 1:1 mixture of (3R)-β-cryptoxanthin (13) and (3R,3'R)-zeaxanthin (5) was crystallized with acetone and hexane. The crystalline product contained 78% of 5 and 22% of 13 while the filtrate from crystallization contained 75% of 13 and 25% of 5. The filtrate was subjected to a second crystallization that allowed the complete removal of 5. The crystalline product from the first crystallization was further crystallized to yield (3R,3'R)-zeaxanthin (5) without any contamination with 13.

Example 6

Separation of (3R,6'R)-α-Cryptoxanthin from (3R,3'R,6R)-Lutein 100 mg of a 1:1 mixture of (3R,6'R)-α-cryptoxanthin (9) and (3R,3'R,6'R)-lutein (1) was subjected to two consecutive Soxhlet extractions with pentane or hexane to yield (3R,6'R)-α-cryptoxanthin (9) in 98% purity while (3R,3'R,6'R)-lutein (1) was only partially extracted into these hydrocarbon solvents during the first extraction and remained as crystals in the Soxhlet second extraction.

Example 7

Simultaneous Extraction and Saponification of (3R,6'R)-α-Cryptoxanthin Monoesters and Lutein Diesters from Marigold Flower Petals (*Tagete erecta*)

50 g of marigold petals were transferred into a Soxhlet extraction apparatus. The flask was charged with 50 mL of a 1:1 mixture of pentane and methanol (100 mL) and 3 g solid NaOH. The petals were extracted at 30.8° C. After 6 hours the extraction was complete since no additional color could be removed from the petals. The extract was partitioned into ethyl acetate and water and after removal of the aqueous layer the organic layer was washed with water, until it was no longer basic. The solvents were evaporated under reduced pressure and the residue was shown by high performance liquid chromatography (HPLC) to consist of lutein (1, 96%), zeaxanthin (5, 3.5%), and α-cryptoxanthin (9, 0.5%). Crystallization of this mixture with acetone and ethanol gave a mixture of 1 and 5 (99%) that contained only 0.1% of 9. The composition of carotenoids in the filtrate from this crystallization was α-cryptoxanthin (9, 89%), lutein (1, 10%), and zeaxanthin (5, 1%). The filtrate was evaporated under reduced pressure and was subjected to a second crystallization to remove 1 and 5 as orange crystals. The filtrate from this second crystallization contained only α-cryptoxanthin (9). The crystals from the first crystallization were further crystallized to yield a mixture of lutein (1, 98%) and zeaxanthin (5, 2%).

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of at least partially separating at least one monohydroxycarotenoid ester from at least one dihydroxycarotenoid ester, comprising continuously extracting, wherein the continuous extraction is carried out by Soxhlet extraction, the at least one monohydroxycarotenoid ester from a mixture of the at least one monohydroxycarotenoid ester and the at least one dihydroxycarotenoid ester with an alcohol to give an alcoholic solution enriched in the at least one monohydroxycarotenoid ester, wherein the at least one monohydroxycarotenoid ester is a α-cryptoxanthin ester or a β-cryptoxanthin ester, and wherein the at least one dihydroxycarotenoid ester is a zeaxanthin diester or a lutein diester.

2. The method of claim 1, further comprising concentrating the alcoholic solution to give a residue enriched in the at least one monohydroxycarotenoid ester.

3. The method of claim 2, wherein the at least one monohydroxycarotenoid ester residue is subjected to further continuous extraction with an alcohol to give an alcoholic solution enriched in the at least one monohydroxycarotenoid ester.

4. The method of claim 3, further comprising concentrating the alcoholic solution to give a residue further enriched in the at least one monohydroxycarotenoid ester.

5. The method of claim 4, further comprising subjecting the residue further enriched in the at least one monohydroxycarotenoid ester to saponification to give an at least one monohydroxycarotenoid.

6. The method of claim 1, further comprising crystallization of the solution enriched in the at least one monohydroxycarotenoid ester.

7. The method of claim 6, wherein the crystallization occurs in a solvent, wherein the solvent is a mixture of a hydrocarbon and an alcohol or acetone and an alcohol.

8. The method of claim 1, further comprising saponification of the at least one monohydroxycarotenoid ester with a base to provide at least one monohydroxycarotenoid, wherein the saponification is carried out simultaneously with the continuous extraction.

9. The method of claim 1, wherein the mixture of the at least one monohydroxycarotenoid ester and the at least one dihydroxycarotenoid ester is present in the petals of marigold flowers.

10. The method of claim 1, wherein the mixture of the at least one monohydroxycarotenoid ester and the at least one dihydroxycarotenoid ester is present in Chinese Lycium mill.

11. The method of claim 1, wherein the at least one monohydroxycarotenoid ester is (3R) - β-cryptoxanthin esters.

12. The method of claim 1, wherein the at least one monohydroxycarotenoid ester is (3R)-β-cryptoxanthin esters and the at least one dihydroxycarotenoid ester is (3R, 3'R)-zeaxanthin esters.

13. The method of claim 1, wherein the at least one monohydroxycarotenoid ester is (3R, 6'R)-α-cryptoxanthin esters and the at least one dihydroxycarotenoid ester is (3R, 3'R, 6'R)-lutein esters.

14. The method of claim 5, wherein the at least one monohydroxycarotenoid is (3R)-β-cryptoxanthin.

15. The method of claim 1, wherein the alcohol is methanol, ethanol, or 2-propanol.

16. The method of claim 1, wherein the esters are myristates, palmitates, acetates, or mixtures thereof.

17. The method of claim 1, wherein the at least one monohydroxycarotenoid ester is a (3R, 6'R)-α-cryptoxanthin ester or a (3R)-β-cryptoxanthin ester.

18. The method of claim 1, wherein the at least one dihydroxycarotenoid is a (3R,3'R)-zeaxanthin diester or a (3R, 3'R, 6'R)-lutein diester.

* * * * *